United States Patent [19]

Riede et al.

[11] Patent Number: 4,942,181
[45] Date of Patent: Jul. 17, 1990

[54] METHOD OF PROTECTING FISH

[75] Inventors: Urs N. Riede, Freiburg-St. Georgen; Ulrich Spitaler, Freinsheim, both of Fed. Rep. of Germany

[73] Assignee: Rutgerswerke AG, Fed. Rep. of Germany

[21] Appl. No.: 392,710

[22] Filed: Aug. 11, 1989

[30] Foreign Application Priority Data

Sep. 9, 1988 [DE] Fed. Rep. of Germany ....... 3830616

[51] Int. Cl.$^5$ ............................................. A01N 31/00
[52] U.S. Cl. ................................................... 514/730
[58] Field of Search ........................................ 514/730

[56] References Cited

U.S. PATENT DOCUMENTS 2,963,400 12/1960 Ross ........................................ 119/3

OTHER PUBLICATIONS

Chemical Abstracts, vol. 103 (98707d) (1985).
Chemical Abstracts, vol. 104 (6219r), 1986.
Chemical Abstracts, vol. 105 (171313v), 1986.

*Primary Examiner*—Douglas W. Robinson
*Assistant Examiner*—Kevin E. Weddington
*Attorney, Agent, or Firm*—Bierman and Muserlian

[57] ABSTRACT

A method of protecting fish from stress comprising adding to the water in which the fish are living a sufficient amount of a low molecular weight alkali metal humate to prevent stress which decisively lowers the mortality rate.

7 Claims, No Drawings

METHOD OF PROTECTING FISH

STATE OF THE ART

Ornamental or hatchery fish under stress are usually very susceptible to diseases, particularly fungus diseases. Fish, particularly imported ornamental fish, are usually transported in tightly crowded water tanks and are thus subjected to stress which is intensified by an increasing oxygen shortage during the transport and by the ammonia content of the water. As a result, these fish will readily become sick and particularly their resistance to fungus attack decreases, so that during the transport and the first days after their importation, many of these fish perish. The average mortality rate is not satisfactorily lowered by addition of hitherto common prophylactics to the water.

Similar problems exist in commercial fish breeding where milk and roe are scraped off the fish before the spawning process and mixed together in separate spawning basins, the spawn and the developing fish being present in great concentration. Moreover, the prophylactics common until now often contain weakly toxic compounds such as malachite green or methyl blue which when the water is discharged presents pollution of the environment problems.

OBJECTS OF THE INVENTION

It is an object of the invention to provide a novel method of reducing the mortality rate of fish under stress while avoiding environmental problems.

It is another object of the invention to provide a novel method of reducing stress in stressed fish.

These and other objects and advantages of the invention will become obvious from the following detailed description.

THE INVENTION

The novel method of the invention for protecting fish from stress comprising adding to the water in which the fish are living a sufficient amount of a low molecular weight alkali metal humate to prevent stress.

The resistance of fish under stress and therefore, their survival rate, increases enormously when there is added to the water surrounding them essentially low molecular weight alkali metal humates. Particularly, the susceptibility to fungus diseases is greatly reduced. This is surprising inasmuch as commercial preparations which contain humic acid show no such effect.

Natural and synthetic low molecular weight alkali metal humates and methods for their production have been described in U.S. patent applications Ser. No. 162,741 now U.S. Pat. No. 4,918,059 and Ser. No. 162,802 now U.S. Pat. No. 4,921,840 filed Mar. 1, 1988 and Ser. No. 193,957 filed May 13, 1988 which are incorporated herein by reference where these low molecular weight alkali metal humates are effective as medication in the healing of wounds.

Their effectiveness and use as a prophylactic for fish, particularly against fungus diseases, is thus new and surprising. Low molecular weight alkali metal humates are substances soluble in water and are not changed in the aqueous solution. Therefore, the simplest form of use is an aqueous solution which may contain, besides the essential component of the low molecular weight alkali metal humates, still other additives common in aquaristics such as vitamins, trace elements, or protective colloids.

The prophylactic treatment of the fish is best done by adding to the water in which the fish live during or after the transport a sufficient quantity of the alkali metal humates. This can be done in the aquarium in the case of ornamental fish or in the breeding ponds in the case of commercial fish. Furthermore, the humates can be admixed with the water of the spawn kept in the separate basin for breeding or of the ornamental fish just hatched. The concentration of the low molecular weight alkali metal humates ranges form 0.5 to 10 ppm, depending on the hardness of the water. For soft water, or when deionizing substances are used as well, a concentration of 0.8 to 2 ppm is sufficient and it has been found favorable to replenish the humates at intervals of 3 to 5 days.

Another treatment method consists in that the fish under stress, for instance after a transport, are placed for a short time, i.e. 10 to 60 minutes, in a bath which contains the humates. The concentration of the low molecular weight alkali metal humates in the bath should then be higher than for long term treatment and generally, a concentration of 2 to 20 ppm of low molecular weight alkali metal humates in such a bath suffices.

The effect of the humates according to the invention is observable already after a short time. The fish become lively and the typical luster of a healthy fish appears and the survival rate increases significantly. While in some fish shipments, even when using commercial water treatment agents or prophylactics, 30 to 40% of the fish perish within the first eight days after arrival, with the use of the humates, survival rates of 90 to 99% are reached.

In the following examples there are described several preferred embodiments to illustrate the invention. However, it should be understood that the invention is not intended to be limited to the specific embodiments.

EXAMPLES

Groups of 170 fish of different varieties were placed after a transport into three different basins, each containing 70 liters of water and were observed and compared over the course of 7 days. The keeping and feeding conditions were the same in each instance and only the basically identical water was changed by additions as follows: Basin a: no addition, Basin b: 20 ml (prescribed dose) of a commercial prophylactic containing humic acid, Basin c: 3 ml of 2% aqueous solution of a low molecular weight alkali metal humate, prepared according to Ser. No. 193,957 as described infra. After 4 days, an additional 2 ml of the 2% solution were proportioned in. The results after 7 days are listed below:

|  | Basin a | Basin b | Basin c |
|---|---|---|---|
| Variety of fish: | | | |
| Swordtail, golden | | | |
| Number of dead animals | 25 | 19 | 0 |
| Mortality rate (%) | 14.7 | 11.2 | 0 |
| Vitality of the living animals | good | good | very good |
| Fungus attack | mild | mild | none |
| Variety: | | | |
| Platy, red | | | |
| Number of dead animals | 20 | 6 | 1 |
| Mortality rate (%) | 11.7 | 3.5 | 0.6 |
| Vitality of the living animals | moderate | good | good |
| Fungus attack | mild | mild | none |
| Variety: | | | |

| | Basin a | Basin b | Basin c |
|---|---|---|---|
| Red phantom salmon | | | |
| Number of dead animals | 86 | 32 | 10 |
| Mortality rate (%) | 50.5 | 18.8 | 5.7 |
| Vitality of the living animals | poor | moderate | moderate |
| Fungus attack | strong | mild | mild |
| Variety: | | | |
| Guppy, female | | | |
| Number of dead animals | 31 | 18 | 9 |
| Mortality rate (%) | 18.2 | 10.5 | 5.1 |
| Vitality of the living animals | moderate | moderate | good |
| Fungus attack | mild | mild | none |

PREPARATION OF LOW MOLECULAR WEIGHT ALKALI METAL HUMATE 20 kg of humus slurry were predried in a drying oven for 12 hours at 80° C. and then were ground in a mill into 1 to 3 mm large particles and homogenized and standardized. A 1 g sample of the standardized humus slurry was slurried in distilled water and titrated with 0.1M sodium hydroxide and the pH changes were measured potentiometrically. After addition of 6.9 ml of 0.1M sodium hydroxide, a point of change in the range of pH 6 to 6.5 was observed. For that reason, 0.69 mmol of sodium hydroxide per g were considered to be the optimum alkali amount for this standardized humic substance-containing product.

In a stirring unit, 10 kg of standardized humus slurry were slurried in 100 liters of distilled water and while being stirred, 117 g of gaseous $NH_3$ were slowly introduced into the suspension. The pH value of the suspension, which during this process was continuously controlled, increased from original 3.9 steadily to 6.3. Beginning with this value at the latest, the addition of the ammonia was throttled so that the pH value remained in the region of 6.3 to 6.5, i.e. the quantity of the added alkaline-acting substance corresponded to that used in the same period in the neutralization of the complex humic substances. Following the addition of $NH_3$ which was completed after 70 minutes, stirring continued for an additional one hour. The stirrer was then switched off and the suspended solid matter settled as slurry at the bottom of the vessel. The supernatant brown solution was decanted and centrifuged directly in a separator at $9,000 \times g$. The resulting purified solution was subjected to ultrafiltration with an ultrafilter of pore width 100,000 D to obtain a dark brown solution with a 2.1% content of an ammonium huminate fraction with an average molecular weight of 1,000 and a range of 300 to 1500.

Various modifications of the method of the invention may be made without departing from the spirit or scope thereof and it is to be understood that the invention is intended to be limited only as defined in the appended claims.

What we claim is:

1. A method of protecting fish from stress due to increasing oxygen shortage and/or an increase in ammonia content of the water comprising adding to the water in which the fish are living a sufficient amount of low molecular weight alkali metal huminate with an average molecular weight of 1000 and a range 300 to 1500 to prevent stress.

2. The method of claim 1 wherein the alkali metal humate is added to the spawn.

3. The method of claim 1 wherein the concentration of the alkali metal humate is 0.5 to 10 ppm.

4. The method of claim 1 wherein the concentration of the alkali metal humate is 0.8 to 2 ppm.

5. A method of rejuvenating fish subjected to stress due to increasing oxygen shortage and/or an increase in ammonia content of the water comprising placing the stressed fish for a short period of time in water containing an amount of a low molecular weight alkali metal huminate with an average molecular weight of 1000 and a range 300 to 1500 sufficient to relieve stress.

6. The method of claim 5 wherein the concentration of alkali metal humate is 2 to 20 ppm.

7. The method of claim 5 wherein the period of time is 10 to 60 minutes.

* * * * *